US010299768B2

(12) United States Patent
Gardner et al.

(10) Patent No.: US 10,299,768 B2
(45) Date of Patent: May 28, 2019

(54) BIOPSY SAMPLER AND SAMPLE COLLECTOR

(71) Applicant: SNPSHOT TRUSTEE LIMITED, Auckland (NZ)

(72) Inventors: Michael Stuart Gardner, Auckland (NZ); Roy Victor Bladen, Auckland (NZ)

(73) Assignee: SNPSHOT Trustee Limited, Auckland (NZ)

(*) Notice: Subject to any disclaimer, the term of this patent is extended or adjusted under 35 U.S.C. 154(b) by 343 days.

(21) Appl. No.: 15/030,211

(22) PCT Filed: Oct. 17, 2014

(86) PCT No.: PCT/IB2014/065396
§ 371 (c)(1),
(2) Date: Apr. 18, 2016

(87) PCT Pub. No.: WO2015/056228
PCT Pub. Date: Apr. 23, 2015

(65) Prior Publication Data
US 2016/0270769 A1 Sep. 22, 2016

(30) Foreign Application Priority Data

Oct. 18, 2013 (NZ) .......................... 616807
Jun. 5, 2014 (NZ) .......................... 625902
Jun. 5, 2014 (NZ) .......................... 625904

(51) Int. Cl.
*A01K 11/00* (2006.01)
*A61B 10/00* (2006.01)
(Continued)

(52) U.S. Cl.
CPC .......... *A61B 10/0266* (2013.01); *A01K 11/00* (2013.01); *A01K 11/003* (2013.01);
(Continued)

(58) Field of Classification Search
CPC ........ A61B 10/0266; A61B 2010/0208; A61B 2503/40
See application file for complete search history.

(56) References Cited

U.S. PATENT DOCUMENTS 4,976,925 A  12/1990  Porcher
6,631,650 B1  10/2003  Espinosa
(Continued)

FOREIGN PATENT DOCUMENTS

AU  2009329486  11/2014
CN  1275894  12/2000
(Continued)

OTHER PUBLICATIONS

Office Action from the US Patent and Trademark Office for U.S. Appl. No. 14/896,325 dated Sep. 27, 2018 (18 pages).
(Continued)

*Primary Examiner* — Sean P Dougherty
(74) *Attorney, Agent, or Firm* — Michael Best & Friedrich LLP

(57) ABSTRACT

A biopsy sampler comprising a penetration zone for receiving a part of an organism, a ram actuated to move along a path between a withdrawn position and an advanced position, a sample collector that cuts a biopsy sample from tissue in the penetration zone, and a container that receives the sample collector, the sample collector and the container being initially located on opposite sides of the penetration zone, a disposable shield initially located between the ram in the withdrawn position and the penetration zone, advance action of the ram to the advanced position bringing together the sample collector and container, and bringing the disposable shield into the penetration zone, withdrawal action of the ram to the withdrawn position withdrawing the disposable shield, leaving the tissue free to leave the penetration
(Continued)

zone, such that in use in collecting a sample the shield contacts tissue surfaces and while the ram does not.

13 Claims, 23 Drawing Sheets

(51) Int. Cl.
*A61B 10/02* (2006.01)
*A61B 90/00* (2016.01)

(52) U.S. Cl.
CPC ........ *A01K 11/006* (2013.01); *A61B 10/0096* (2013.01); *A61B 10/0283* (2013.01); *A61B 2010/0208* (2013.01); *A61B 2010/0225* (2013.01); *A61B 2090/081* (2016.02); *A61B 2503/40* (2013.01); *A61B 2562/08* (2013.01)

(56) References Cited

U.S. PATENT DOCUMENTS

| | | |
|---|---|---|
| 6,659,338 B1 | 12/2003 | Dittmann |
| 6,696,923 B2 | 2/2004 | Ishii et al. |
| 6,753,759 B2 | 6/2004 | Stegmaier et al. |
| 6,947,866 B2 | 9/2005 | Staab |
| 6,968,639 B2 | 11/2005 | Destoumieux |
| 7,235,055 B2 | 6/2007 | Pfistershammer |
| 7,467,760 B2 | 12/2008 | Schieli et al. |
| 7,528,725 B2 | 5/2009 | Stewart |
| 7,764,177 B2 | 7/2010 | Stewart |
| 7,764,181 B2 | 7/2010 | Stewart et al. |
| 7,791,409 B2 | 9/2010 | Arrigo |
| 7,936,272 B2 | 5/2011 | Stewart |
| 8,070,757 B2 | 12/2011 | Eadie |
| 8,159,291 B2 | 4/2012 | Arrigo |
| 8,361,416 B2 | 1/2013 | Berner |
| 8,581,705 B2 | 11/2013 | Stewart |
| 8,668,655 B2 | 3/2014 | Destoumieux |
| 8,763,287 B2 | 7/2014 | Hilpert |
| 8,854,188 B2 | 10/2014 | Stewart |
| 2002/0120216 A1 | 8/2002 | Fritz et al. |
| 2004/0103567 A1 | 6/2004 | Destoumieux |
| 2004/0167429 A1 | 8/2004 | Roshdieh |
| 2004/0167430 A1 | 8/2004 | Roshdieh |
| 2004/0232323 A1 | 11/2004 | Bosco et al. |
| 2005/0038355 A1 | 2/2005 | Gellman et al. |
| 2005/0228310 A1 | 10/2005 | Pfistershammer |
| 2005/0272057 A1 | 12/2005 | Abrahamsen |
| 2007/0239067 A1 | 10/2007 | Hibner |
| 2008/0064983 A1 | 3/2008 | Stromberg |
| 2008/0170967 A1 | 7/2008 | Itoh |
| 2008/0227662 A1 | 9/2008 | Stromberg |
| 2008/0228105 A1* | 9/2008 | Howell ............... A01K 11/003 600/567 |
| 2009/0270878 A1 | 8/2009 | Eadie |
| 2010/0016758 A1 | 1/2010 | Hilpert |
| 2010/0160830 A1 | 6/2010 | Schmiedl |
| 2010/0168616 A1 | 7/2010 | Schraga et al. |
| 2010/0210011 A1 | 8/2010 | Hilpert |
| 2010/0286556 A1* | 11/2010 | Decaluwe ............ A01K 11/003 600/567 |
| 2010/0291662 A1 | 11/2010 | Berner |
| 2011/0127177 A1 | 6/2011 | Hostettler |
| 2011/0269228 A1 | 11/2011 | Decaluwe |
| 2011/0295148 A1 | 12/2011 | Destoumieux |
| 2012/0010526 A1 | 1/2012 | Hilpert |
| 2012/0016263 A1 | 1/2012 | Hilpert |
| 2013/0040358 A1 | 2/2013 | Woods |
| 2013/0204159 A1 | 8/2013 | Destoumieux |
| 2013/0211287 A1 | 8/2013 | Decaluwe |
| 2013/0211416 A1 | 8/2013 | Teychene |
| 2014/0249449 A1 | 9/2014 | Hilpert |
| 2015/0112225 A1 | 4/2015 | Prow et al. |
| 2015/0226646 A1 | 8/2015 | Lardi et al. |
| 2016/0007567 A1 | 1/2016 | Decaluwe et al. |

FOREIGN PATENT DOCUMENTS

| | | |
|---|---|---|
| CN | 102933157 | 2/2013 |
| CN | 103052313 | 4/2013 |
| DE | 19835014 | 8/1999 |
| DE | 20022647 | 1/2002 |
| EP | 0016236 | 10/1980 |
| EP | 982688 | 3/2000 |
| EP | 1014861 | 7/2000 |
| EP | 1060662 | 12/2000 |
| EP | 1318718 | 6/2003 |
| EP | 1781086 | 9/2007 |
| EP | 1920651 | 5/2008 |
| EP | 1809096 | 2/2009 |
| EP | 2066170 | 6/2009 |
| EP | 2068718 | 6/2009 |
| EP | 2160093 | 3/2010 |
| EP | 2168207 | 3/2010 |
| EP | 2249966 | 11/2010 |
| EP | 2265109 | 12/2010 |
| EP | 2307136 | 4/2011 |
| EP | 2355653 | 8/2011 |
| EP | 2378863 | 10/2011 |
| EP | 2384618 | 11/2011 |
| EP | 2384619 | 11/2011 |
| EP | 1718142 | 10/2012 |
| EP | 2579781 | 4/2013 |
| EP | 2579782 | 4/2013 |
| EP | 2597944 | 6/2013 |
| EP | 2736324 | 6/2014 |
| EP | 2770819 | 9/2014 |
| FR | 2939281 | 6/2010 |
| GB | 2358061 | 7/2001 |
| GB | 2482036 | 1/2012 |
| IN | 201200015 | 5/2012 |
| JP | 2006026227 | 2/2007 |
| JP | 2012511310 | 5/2012 |
| JP | 2012514201 | 6/2012 |
| JP | 2012526966 | 11/2012 |
| JP | 2013079859 | 5/2013 |
| NZ | 503521 | 12/2002 |
| NZ | 575341 | 1/2012 |
| NZ | 593039 | 12/2012 |
| NZ | 596853 | 2/2014 |
| NZ | 608927 | 11/2014 |
| SU | 946387 | 7/1982 |
| WO | 200051496 | 9/2000 |
| WO | 2001040762 | 6/2001 |
| WO | 2002023980 | 3/2002 |
| WO | WO 2002039810 | 5/2002 |
| WO | WO 2005101273 | 10/2005 |
| WO | 2006000869 | 1/2006 |
| WO | 2007013820 | 2/2007 |
| WO | 2008037802 | 4/2008 |
| WO | 2008040692 | 4/2008 |
| WO | 2008101497 | 8/2008 |
| WO | 2009010658 | 1/2009 |
| WO | WO 2009008861 | 1/2009 |
| WO | 2009046957 | 4/2009 |
| WO | 2009095178 | 8/2009 |
| WO | 2009127541 | 10/2009 |
| WO | WO 2009120206 | 10/2009 |
| WO | 2010012446 | 2/2010 |
| WO | 2010066475 | 6/2010 |
| WO | 2010070129 | 6/2010 |
| WO | 2010070130 | 6/2010 |
| WO | WO 2010066475 | 6/2010 |
| WO | WO 2010070130 | 6/2010 |
| WO | WO 2011044585 | 4/2011 |
| WO | 2011073359 | 6/2011 |
| WO | 2011154233 | 12/2011 |
| WO | 2011154510 | 12/2011 |
| WO | 2012013429 | 2/2012 |
| WO | 2013014034 | 1/2013 |
| WO | 2013060690 | 5/2013 |
| WO | WO 2013155557 | 10/2013 |
| WO | 2014153181 | 9/2014 |
| WO | WO 2015014461 | 2/2015 |

(56) References Cited

FOREIGN PATENT DOCUMENTS

| WO | WO 2015158787 | 10/2015 |
| WO | WO 2016016204 | 2/2016 |
| WO | WO 2016073754 | 5/2016 |

OTHER PUBLICATIONS

Office Action from the US Patent and Trademark Office for U.S. Appl. No. 14/896,322 dated Jun. 12, 2018 (13 pages).
International Search Report for Application No. PCT/IB2014/065396 dated Feb. 19, 2015 (6 pages).
Written Opinion of the International Searching Authority for Application No. PCT/IB2014/065396 dated Feb. 19, 2015 (7 pages).
International Search Report for Application No. PCT/IB2014/065394 dated Feb. 9, 2015 (3 pages).
International Preliminary Report on Patentability for Application No. PCT/IB2014/065394 dated Feb. 3, 2016 (4 pages).
International Search Report for Application No. PCT/IB2014/065395 dated Feb. 10, 2015 (5 pages).
International Preliminary Report on Patentability for Application No. PCT/IB2014/065395 dated Sep. 2, 2015 (5 pages).
International Search Report for Application No. PCT/IB2014/065397 dated Feb. 26, 2015 (3 pages).
International Preliminary Report on Patentability for Application No. PCT/IB2014/065397 dated Feb. 3, 2016 (4 pages).
International Search Report for Application No. PCT/IB2014/065393 dated Feb. 3, 2015 (6 pages).
International Preliminary Report on Patentability for Application No. PCT/IB2014/065393 dated Feb. 3, 2016 (7 pages).

* cited by examiner

BIOPSY SAMPLER AND SAMPLE COLLECTOR

CROSS-REFERENCE TO RELATED APPLICATIONS

This application is a national stage filing under 35 U.S.C. § 371 of International Application No. PCT/IB2014/065396, filed Oct. 17, 2014, which claims foreign priority to New Zealand Application No. 625904, filed Jun. 5, 2014, New Zealand Application No. 625902, filed Jun. 5, 2014, and New Zealand Application No. 616807, filed Oct. 18, 2013. The entire contents of all four applications are incorporated herein by reference.

FIELD OF THE INVENTION

The invention relates to a biopsy sampler and sample collector.

BACKGROUND OF THE INVENTION

To improve the tracking of livestock and to facilitate DNA testing, tissue samples may be collected from animals. A tissue sample may be taken from an animal at any time and is often taken at the same time as placing an identification tag on the animal. The tissue sample is usually cut from an animal using a tissue sampling device and is placed in a storage container for laboratory analysis.

US patent publications US2011/0295148 and US2013/0204159 describe a tissue sampler in the shape of a clamp and comprising a pair of jaws that move toward each other to take a tissue sample. A cutting element is located in one of the jaws and is forced through an animal's ear, for example, to cut a plug of tissue from the ear as the jaws are clamped together using a first actuation action. A plunger is used to push the tissue sample out of the cutting element and into a storage tube held by the other jaw of the tissue sampler. The storage tube has a closed end and an opposing end. The tube comprises an aperture through which the tissue sample is pushed by the plunger. The plunger remains in the aperture of the storage tube cap to seal the tube before the tube is removed from the device and taken away for analysis.

After the storage tube is removed, the cutting element needs to be removed from the sampler because a different cutting element needs to be used for each tissue sample to prevent contamination of the tissue sample. The cutting element can be automatically ejected through a second actuation action of the sampler. The cutting element is then discarded onto the ground or into a refuse container. The cutting elements are sharp and so handling the cutting element carries a risk of being cut. Discarding the cutting element on the ground also carries this risk.

Cross contamination of repeated contact by a ram of a sampler tool with animal tissue of different animals can also cause problems.

It is an object of the present invention to provide a biopsy sampler and sample collector that addresses the above disadvantages and/or that will at least provide the public with a useful choice.

SUMMARY OF THE INVENTION

In a first aspect the present invention may broadly be said to be a biopsy sampler comprising:

a penetration zone for receiving a part of an organism to be sampled, a ram situated at a first side of the penetration zone able to be actuated to move along a path between a withdrawn position and an advanced position, a sample collector that can cut a biopsy sample from tissue interposed in the penetration zone, and a container that can receive the sample collector, the sample collector and the container being initially located on opposite sides of the penetration zone, a disposable shield initially located between the ram (with the ram in the withdrawn position) and the penetration zone, advance action of the ram from the withdrawn to the advanced position bringing together the sample collector and container at side of the penetration zone away from the ram, and bringing the disposable shield into the penetration zone, withdrawal action of the ram from the advanced position to the withdrawn position withdrawing the disposable shield to the first side of the penetration zone, leaving the tissue free to leave the penetration zone, such that in use in collecting a sample the shield contacts tissue surfaces and the ram does not contact tissue surfaces.

Preferably the disposable shield is a sleeve to receive a leading end of the ram, and protect the leading end of the ram from contacting the tissue surfaces to the extent that the leading end of the ram enters the penetration zone.

Preferably the sleeve is open through to both ends such that the leading end of the ram may act directly on the sample collector or container.

Preferably the disposable shield spaces the ram from the sample collector or container and the ram acts to bring the sample collector and container together by acting on the shield which acts on the sample collector or container.

Preferably the travel of the ram is limited so that the ram cannot enter the penetration zone.

Preferably the disposable shield releasably connects to a leading end of the ram as the ram advances, and disconnects as or before the ram reaches the withdrawn position on withdrawal.

Preferably the sample collector is initially located between the ram and the penetration zone.

Preferably the disposable shield is releasably fitted to the sample collector in an initial condition, and releasably connects to a leading end of the ram as the ram advances, disconnects from the sample collector as the ram begins to withdraw, and disconnects from the ram as or before the ram reaches the withdrawn position on withdrawal.

Preferably the connection of the ram to the shield is stronger than the connection of the shield to the sample collector such that withdrawal of the ram reliably releases the shield from the sample collector.

Preferably the biopsy sampler includes a magazine loading zone between the ram (in the withdrawn position) and the penetration zone, and a magazine locatable in the magazine loading zone, the magazine carrying a plurality of sample collectors to be selectively presented in the path of the ram and be actuated by the ram to be moved from the magazine through the penetration zone, each sample collector being stored in the magazine in association with a respective disposable shield, the disposable shield returning to the magazine on withdrawal of the ram after actuation.

Preferably the shield releases from the ram upon full withdrawal of the shield into the magazine and by continuing withdrawal motion of the ram.

Preferably the ram projects through an aperture in the advanced position but not in the withdrawn position, and the shield does not fit into the aperture so that during withdrawal of the ram with an attached shield, the shield butts against the periphery of the aperture and the further withdrawal of the ram disengages the shield from the ram.

Preferably the shield has a first connection interface with the collector, the shield has a second connection interface with the ram and the collector has a connection interface to a vial or cover that is made good upon actuation of the ram to take a sample, the collector to vial (or cover) interface having a greater disconnection force than the shield to collector interface, and the shield to collector interface having a lower disconnection force than the shield to ram interface.

Preferably the sample collector includes a body and a plunger actuable within the body, actuation of the plunger releasing a sample from the sample collector, and neither the ram nor the spacer actuate the plunger in pressing the sample collector through the penetration zone.

Preferably the disposable shield is longer than the breadth of the penetration zone.

In a further aspect the present invention may broadly be said to be a biopsy sampling product comprising a magazine storing a plurality of sample collectors having a cutter at one end that can cut a biopsy sample from tissue and for each stored collector, a disposable shield in line with the collector at the end away from the cutter.

In a further aspect the present invention may broadly be said to be a biopsy sampling product comprising a sample collector having a cutter at a first end that can cut a biopsy sample from tissue and a disposable shield removably connected to an end of the sample collector opposite the first end.

Preferably the disposable shield is greater than 50% of the length of the sample collector.

Preferably the disposable shield includes connection features at an end away from the end which connects to the sample collector.

Preferably the sample collector includes a body carrying the cutter at one end, and a plunger housed within the body, the plunger actuable from the end of the sample collector that is connected to the shield, and the shield is connected to the body and not to the plunger, and pressure on the shield toward the body does not cause the shield to act on the plunger.

Preferably the sampler is to hold a (i) storage container as herein described and a shield as herein described and a sample collector as herein described to take and hold and store a biopsy sample from an organism said collector comprising a punch that includes a cutter with a cutting edge formed at a cutting end of the punch to remove and retain a biopsy sample the tool comprising a body carrying a ram to drive the collector and able to be actuated for move along a path relative the body between a first position aligned to drive the collector from a primed position separated from said container with part of said organism intermediate, and push the collector and shield through part of said organism and a second position where said cutter has been so pushed through by said ram, to remove a sample from said organism and into the storage container, the collector retained after sampling at the passage and plugging the passage into the storage container, the shield having moved back towards the ram's first/retracted position.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

The entire disclosures of all applications, patents and publications, cited above and below, if any, are hereby incorporated by reference.

Any reference to prior art documents in this specification is not to be considered an admission that such prior art is widely known or forms part of the common general knowledge in the field.

BRIEF DESCRIPTION OF THE DRAWINGS

Preferred forms of the invention will now be described by way of example only and with reference to the accompanying drawings, in which:

FIG. 2a is a perspective view of one form of punch for a collector;

FIG. 2b is a side view of the punch of FIG. 2a;

FIG. 2c is an end view showing the pushing end of the punch of FIG. 2a;

FIG. 2d is a side view of the punch taken along line A-A of FIG. 2c;

FIG. 2e is an end view showing the cutting end of the punch of FIG. 2a;

FIG. 3b is a side view of the body of FIG. 3a;

FIG. 3c is a cross-sectional side view of the body taken along line A-A of FIG. 3a;

FIG. 3d is an end view of the closed second end of the body of FIG. 3a;

DETAILED DESCRIPTION OF PREFERRED FORMS OF THE INVENTION

Figure 1A:
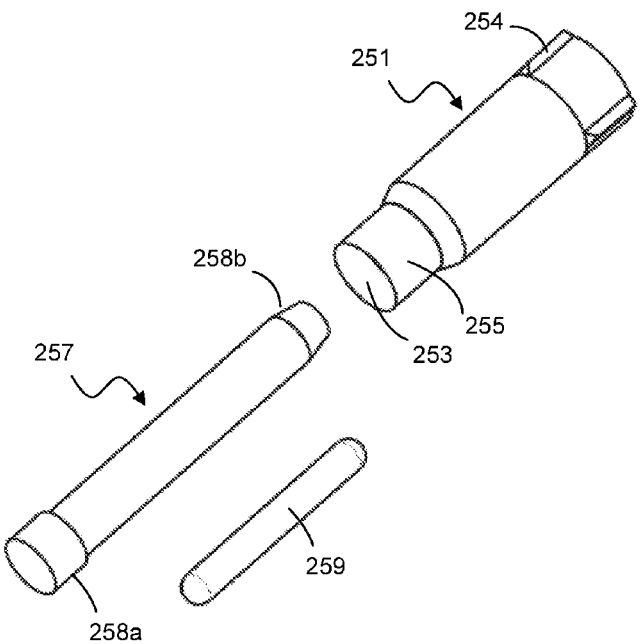
FIG. 1a is an exploded view of one form of collector.

Reference will now be made to a biopsy sampler and sample collector storage container to store biopsy samples. Such samples may be from an organism such as plants or animals particularly, including pigs, goats, cattle, sheep, poultry, and fish. In a preferred form the sample is taken from the ear of an animal. Together the collector and container can collect and store a biopsy sample for later analysis.

The collector will first be described.

FIGS. 1a to 1g show a preferred form of a collector 250. The collector can be used with the tissue sampler as will herein after be described.

The collector 250 comprises a punch 251 having a body with a cutter 255 at a cutting end 252a of the punch 251. The punch 251 also has an opposing pushing end 252b. The body of the punch 251 preferably has a slot or bore 253. The bore 253 extends from one end of the punch to the other. It preferably extends along the length of the punch between the cutting end and the pushing end, as shown in FIGS. 2a to 2e.

Preferably, the punch has an elongate straight body and the bore is centrally located within the body of the punch.

In one form, the outer surface of the body of the punch comprises guides in the form of one or more projections or recesses to help locate the punch within a cap of a storage container as will be described later. In the embodiment shown in FIGS. 2a to 2d, the guides comprise three evenly spaced ribs 254 that project from the pushing end 252b of the punch. A lead-in 254a may also be provided.

A cutter 255 is provided at the cutting end 252a of the punch to remove a sample from an organism. The cutter may be attached to the punch or it may be integral with the punch so that the cutter and punch are formed as a single part. The cutter 255 may be cylindrical. It may alternatively be of another shape suitable to remove a sample. The sample may for example be taken from the tip of the ear of an animal and the cutter may as a result be U or V shaped or other shape. It need not take a core sample but an edge sample instead. Being of a hollow section such as cylindrical does offer the added benefit of being able to retain the sample, as a plug, by the cutter. The cutter can remove a sample plug that ends up sitting in the cutter.

A free end of the cutter 255 is presented to form a cutting edge 255a. The cutter 255 preferably extends from and surrounds one end of the bore 253 of the punch at the cutting end of the punch body to form a projecting surrounding wall or walls. Preferably, the bore 253 of the punch is cylindrical so that the cutting edge is substantially circular. A sample holding section 256 is formed by the cutter, preferably within the projecting wall(s) of the cutter. In this way, the cutter provides a sample holding section 256 such as a bore. The bore is a blind bore terminated by the end of the plunger 257. It is aligned with the bore formed in the body of the punch. For the sake of simplicity, the bore 253 of the punch, when referred to in this specification, should be interpreted to include the bore formed in the body of the punch and the bore formed in the cutter because the two are preferably contiguous.

An optional plunger 257 may be held by the punch. If so provided it is located by the bore 253 of the punch and forms part of the collector. If not provided, the punch may not have a bore. In one form the plunger protrudes at least partially from the punch. In other forms it is contained entirely within the bore. Being within the bore helps protect it and prevent tampering therewith at least unless an appropriate tool is used.

The plunger has a first end 258a and an opposing second end 258b.

The plunger 257 can be seen to extend into the bore 253 of the punch 251. The fit of the plunger in the bore is snug yet allowing for the plunger to slide relative the punch. In the preferred form the plunger outer surface is contiguous the inner surface of the bore. This ensures that a seal is created there between, preventing ingress of contaminants from the pushing end of the punch to the cutting end, through the bore.

The plunger and punch are in a sliding relationship with each other whether it is using a bore and pin like relationship or other. They are in a sliding relationship so that the sample can be pushed off the cutter.

The plunger in the preferred form extends into the bore of the punch and can push a plug of sample tissue from the sample holding section 256. This pushing may be to push the sample into a storage container with which the collector becomes associated after sample taking. It may occur at the time of sampling or well after such as in the laboratory at where the sample will be processed. In the lab the sample may be pushed off the cutter and into a test tube after the container has been removed from the collector retaining cap.

Figure 1B:
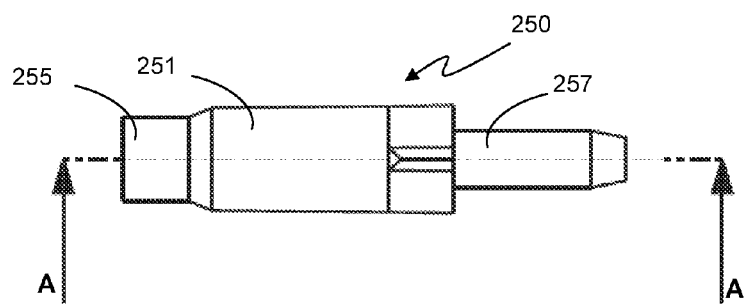
FIG. 1b is a side view of one form of the collector.
Figure 1C:
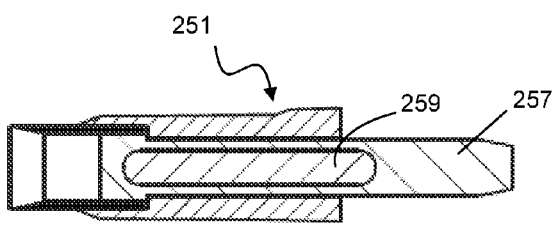
FIG. 1c is a cross-sectional side view of the collector taken along line A-A of FIG. 1b.
Figure 1D:
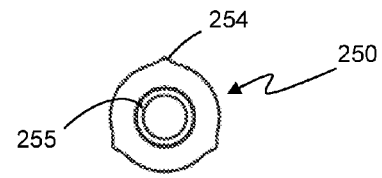
FIG. 1d is an end view of the collector of FIG. 1b.
Figure 1E:
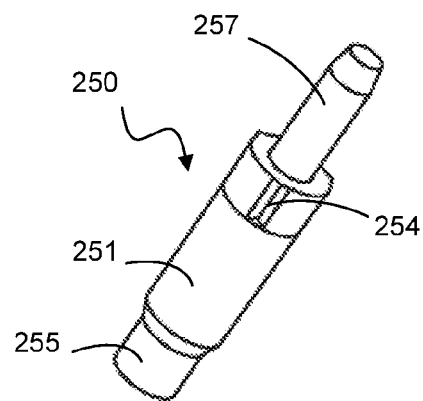
FIG. 1e is a perspective view of another form of the collector.
Figure 1F:
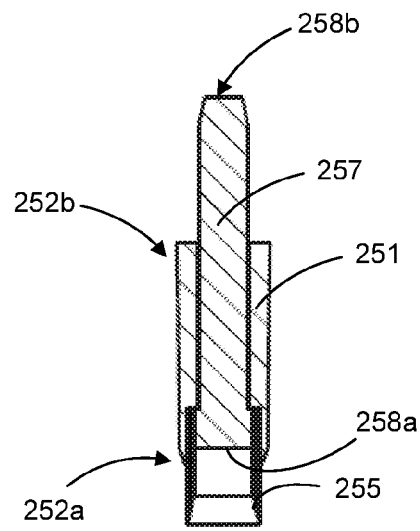
FIG. 1f is a cross-sectional side view of the collector of FIG. 1e.
Figure 1G:
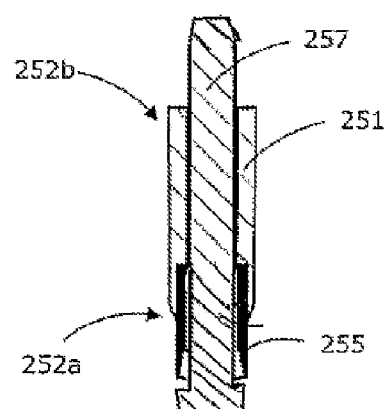
FIG. 1g is a view of the collector in a condition where the plunger is actuated.
Figure 2E:
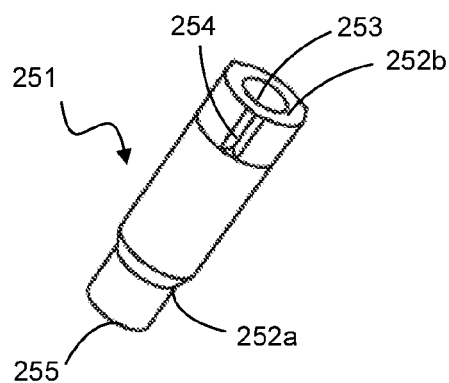
Figure 2E:
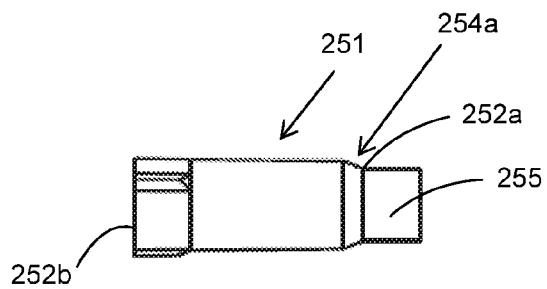
Figure 2E:
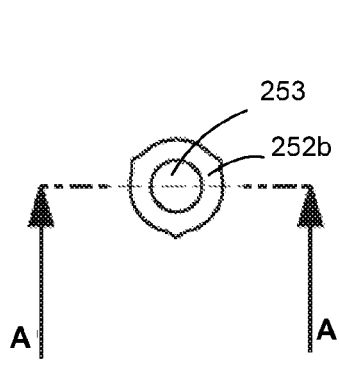
Figure 2E:
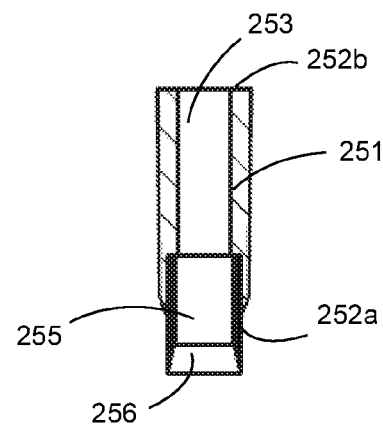
Figure 2E:
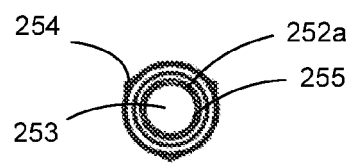
Figure 3A:
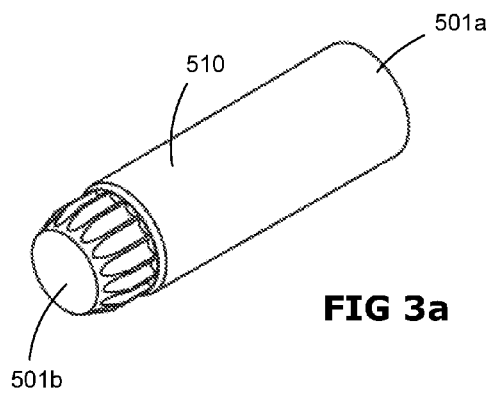
FIG. 3a is a perspective view of one form of storage body according to the invention.
Figure 3B:
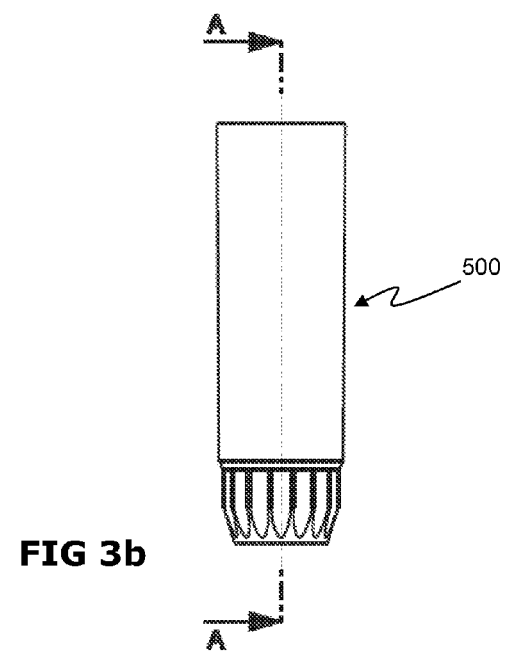
Figure 3C:
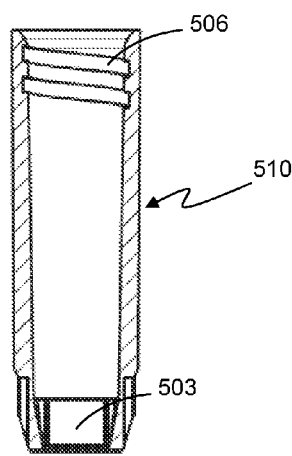
Figure 3D:
Figure 3E:
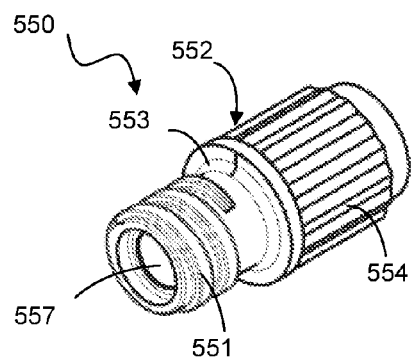
FIG. 3e is a perspective view of one form of cap for a storage container according to the invention.
Figure 3F:
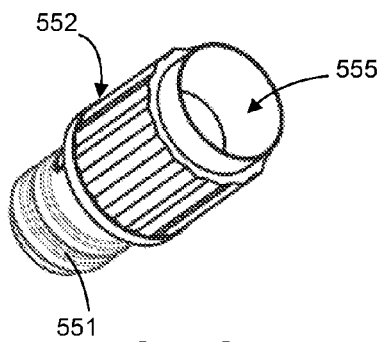
FIG. 3f is another perspective view of the cap of FIG. 3e.
Figure 3G:
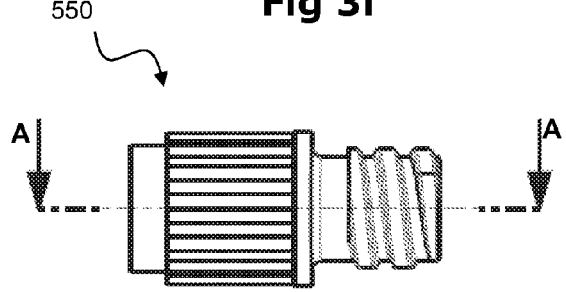
FIG. 3g is a side view of the cap of FIG. 3e.
Figure 3H:
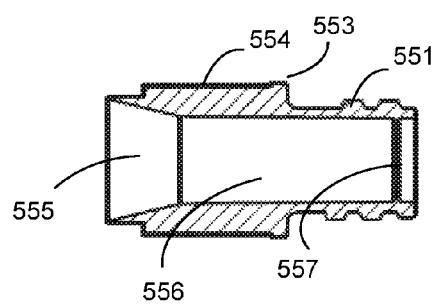
FIG. 3h is a cross-sectional side view of the cap of FIG. 3g.

The plunger is able to be positioned in an active position as shown in FIG. 1b and be moved to a plunged position as seen in FIG. 1g.

To assist with the release of the tissue sample, the first end of the plunger may be enlarged and may comprise an anti-stick surface formed of a non-stick material, such as Teflon™. The plunger may be depressed and pushed towards the sample holding region after the container has been removed from a tissue sampler.

Although in a preferred form the punch is substantially tubular and the plunger is substantially cylindrical, it is envisaged that the punch and plunger may be of any suitable complementary shape. For example, the bore of the punch may have a square cross-section and the plunger may also have a square cross-section of a slightly smaller size so that the plunger can slide within the bore of the punch. It should be appreciated that the cutting edge of the cutter could also be of any suitable shape and size to cut a tissue sample that fits within the storage container for receiving the sample. For example, the cutting tip may be square, oval, star shaped or irregularly shaped.

In the preferred form the collector is held by a tissue sampler as will herein after be described that also holds the storage container at the time of sampling.

In one form, as shown in FIGS. 3a to 3d, the storage container 500 comprises a container body 510 having an open first end 501a and a closed second end 501b, which forms the base of the container body, although it should be appreciated that the container body will not always be oriented so that the base is at the bottom of the container body.

In one form, the container body 510 comprises a tissue sample chamber 503 at its base to receive a tissue sample. A preservative 505 may be provided in the tissue chamber.

Optionally, the storage container comprises a cap that attaches to the open first end of the container body to seal the container body. Alternatively, the cap may have an aperture formed therein through which a tissue sample can pass to be placed in the container body. In this form, the cap is attached to the container body, but does not fully seal the container body.

Preferably, the container body comprises a threaded region at or near its first end that meshes with a threaded region of the cap to allow the cap to be screwed onto and off the storage container body. Alternatively, the cap is attached to the open end of the container body with a snug fit. In yet another form, the cap comprises a lip on its inner surface that nests within a channel that surrounds the outer surface of the container body near the open end of the container body. As will be appreciated, the cap may be attached to the container body in any other suitable arrangement and these are just some examples that could be used. A threaded relationship is preferred because it assists in cap removal.

In one form, as shown in FIGS. 6a to 6e, the storage container 500 comprises a cap 550 that is screwed onto a threaded region 506 of the container body 510, as described above. In particular, the cap comprises a threaded shaft 551 that is adapted to engage with a threaded interior region 506 of the storage container 500 so that a first end of the shaft projects toward the base 501b of the body. Alternatively, the shaft may have a threaded bore that is adapted to engage with a threaded exterior region of the container body so that a first end of the shaft projects toward the end of the container body. A collar 552 extends from the opposing second end of the threaded shaft. The collar 552 comprises an outwardly projecting annular flange 553 and a guide wall 554 that extends from the periphery of the flange 553 in a direction away from the shaft 551 to form a substantially cylindrical wall.

A recess 555 aligns with a passage 556 that is centrally located through the cap. The cap also comprises a breakable seal 557, which may be in the form of a membrane, or the like, that extends laterally across the cap. The seal may be formed integrally with the collar and shaft of the cap so that the entire cap is made as one part. Preferably, the seal is located at or near a first end of the shaft, but in other forms, the seal may be located within the collar of the cap or in any other suitable location. The seal 557 may be of any suitable material, such as polypropylene, rubber, polyethylene, or the like. When the cap 550 is attached to the body of a container body 510 so that the first end of the shaft projects into the body, the seal 557 extends across the body to seal the first end 501a of the container body. Preferably, the cap 550 also comprises a second seal 558, such as an o-ring, that fits over the outside of the threaded shaft 551 and abuts the collar 552 of the cap. In this form, when the cap is attached to the body of a storage container, the second seal is positioned between the first end 501a of the body and the collar 552 of the cap 550 to seal the connection between the cap and the body. In this arrangement, the cap can be screwed onto a sterile body to hermetically seal the containment region in the body. The interior of the body can remain sterile until the seal is broken and a tissue sample is placed in the container body.

In the preferred form the cap and the container body are engaged to each other in a tamper evident manner. This allow for detection of the removal of the cap from the container body. Preferably the tamper evident manner provides some visual evidence of tampering. For example, connecting tabs may be provided between the collar and an attachment ring of the cap that is securely attached to the tube. In this form, if the cap is twisted away from the attachment ring (such as by unscrewing the cap from the body), the connecting tabs break to indicate that the storage container has been tampered with. A shrink wrap over the container cap interface may be used as a tamper evident indicator. A sticker may be used that will pull apart when the cap and container are separated. A frangible ring or the like could be used also.

In a preferred embodiment connecting tabs 701 are secured at one end to a collar 705 on the cap or to the cap itself. The connecting tabs 701 are also secured in a frangible manner at another end to an attachment ring 703. The container 500 comprises complementary engaging features 702 which complement the shape of the connecting tabs 701. In one embodiment a ring of engaging features 702 are spaced about the periphery of the container 500. The connecting tabs 701 are configured to fit between the spaces of the adjacent engaging features 702. The attachment ring 703 is designed to not be able to pass over the top of the engaging features 702. As such when the container 500 is locked on the cap 550 the engaging features 702 and the connecting tabs 701 engage with each other to prevent any twisting motion, whilst the attachment ring 703 prevents any translational movement of the cap from the container 500. The cap 550 is secured to the container 500 during production or manufacture. In one embodiment the attachment ring 703 is allowed to slide overtop of the engaging features 702 in one direction (towards each other), but not in another direction (away from each other).

Figure 14:
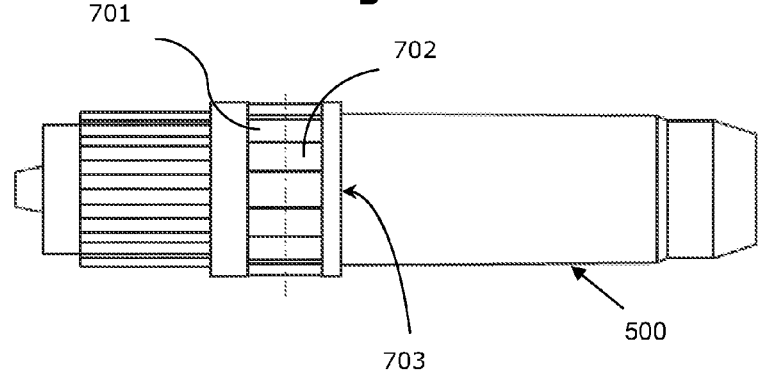
FIG. 14 is a side view of FIG. 13 in an assembled condition.
Figure 15:
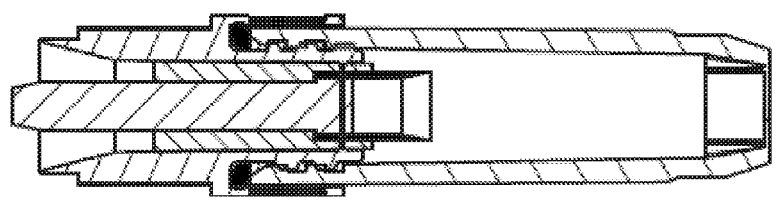
FIG. 15 is a side cross section of FIG. 14.
Figure 16:
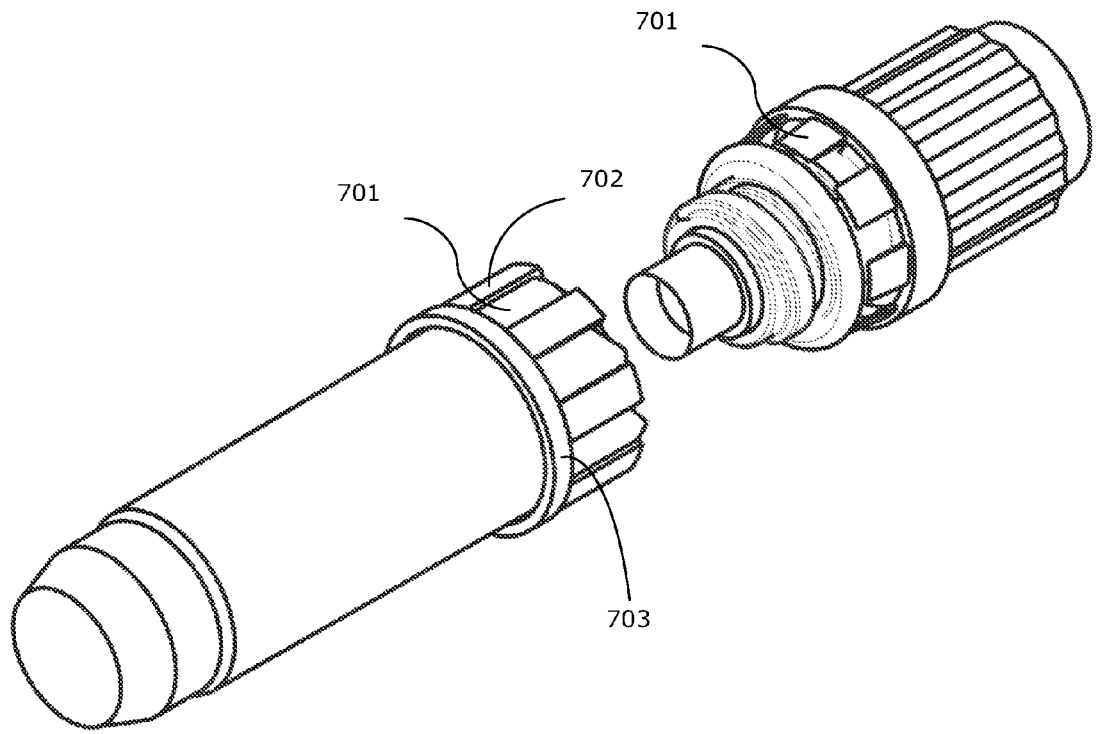
FIG. 16 is a perspective view of a tamperproof collector and associated storage container with the tamperproof seal broken.
Figure 17:
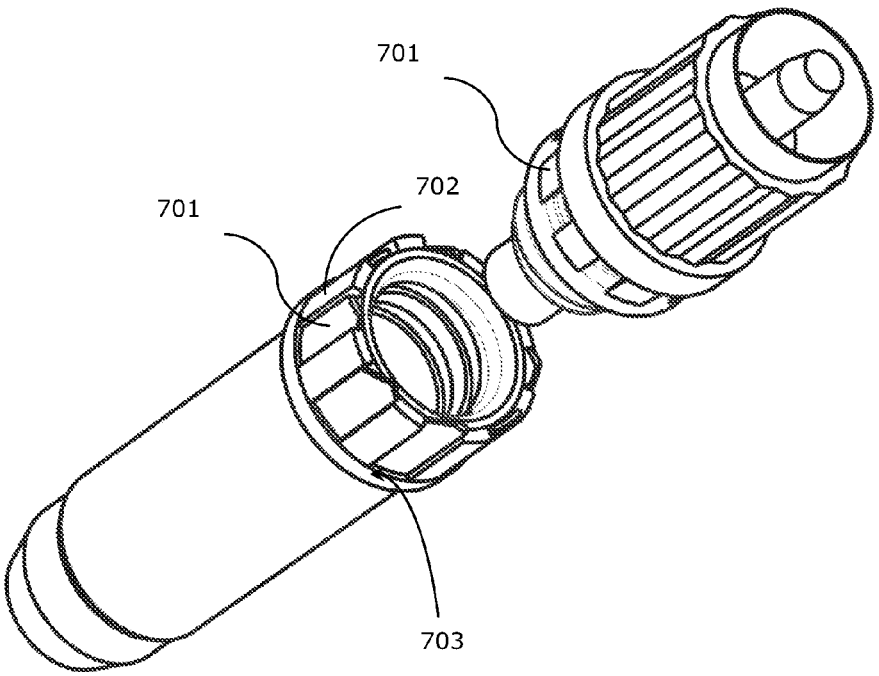
FIG. 17 is another perspective view of FIG. 16.

The cap 550 and the storage container 500 are shown threadingly engaged in FIGS. 14 and 15. To remove the cap 550, the cap must be rotationally turned and the connecting tabs 701 will frangibly disconnect from either the attachment ring 703 or the collar 705. This frangible disconnection is a visual cue that allows a user to identify whether the storage container 500 has been opened. FIGS. 16 and 17 show a perspective view of a frangibly disconnected storage container 500 and cap 550. Once a frangible disconnection has occurred, the cap 500 can be removed from the container.

Figure 4:
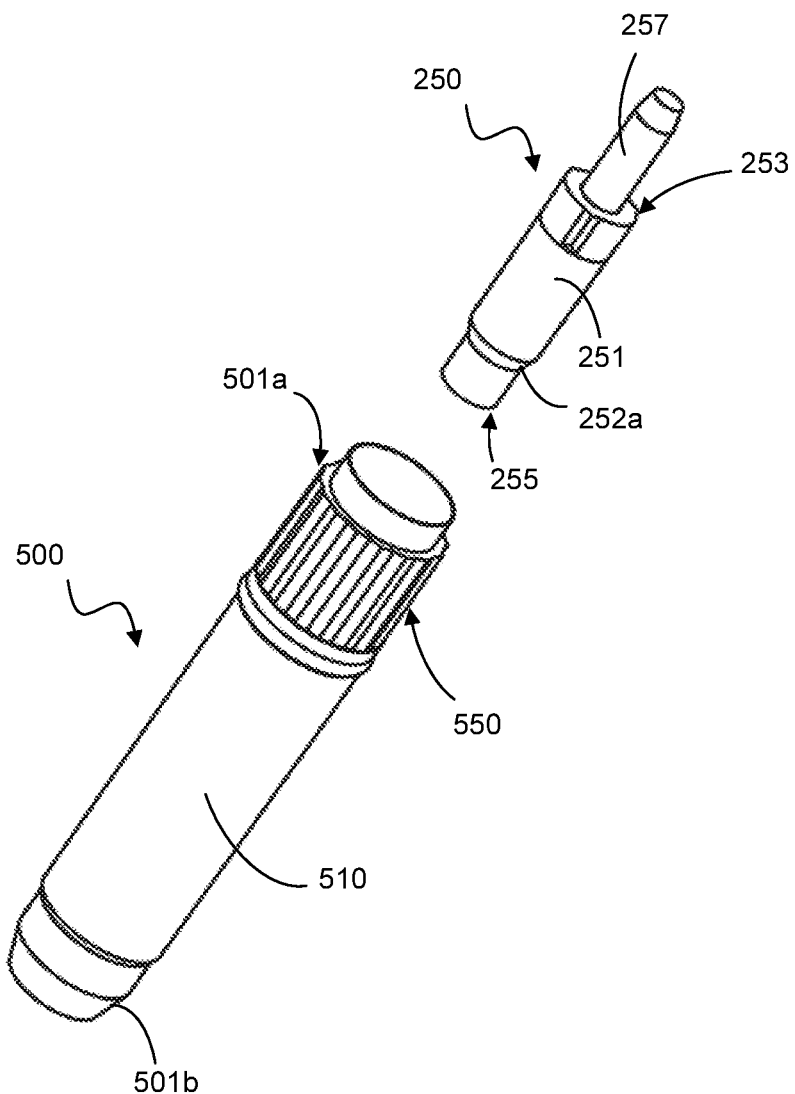
FIG. 4 is a perspective view of one form of the collector before being inserted into a storage container.

The storage container and collector are aligned at the time of sampling as shown in FIG. 4. They are separated prior to sampling so that part of the item from which the sample is to be removed can be located there between.

As will now be described, the collector and the storage container may be so held for sampling purposes by a sampler. The sampler is described in our co-pending international application PCT/NZ2014/000106 which by way of cross reference is hereby incorporated. Pneumatically or electrically operated samplers or other are also envisaged as being adaptable for use with the present invention.

Figure 5:
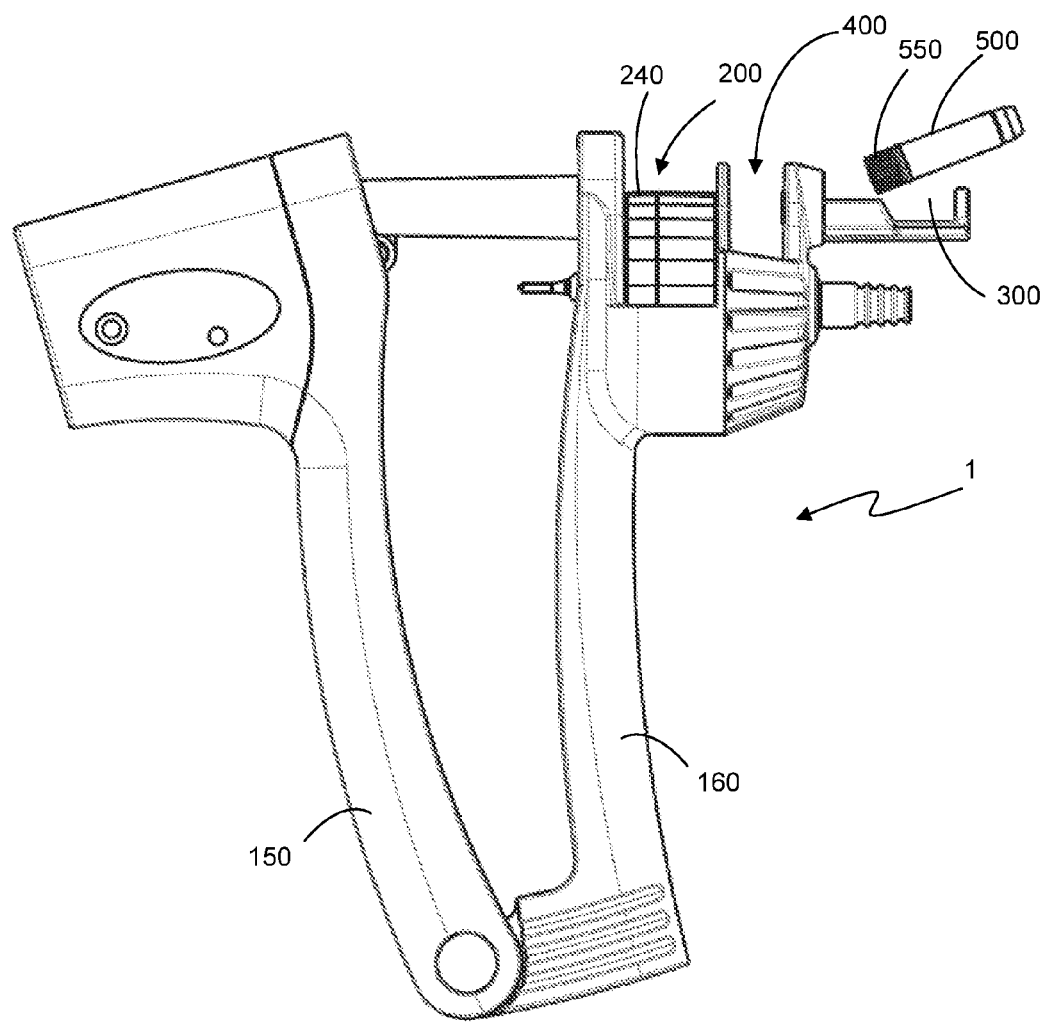
FIG. 5 is a side view of one form of tissue sampler in which a storage container is about to be placed into the tissue sampler.
Figure 5A:
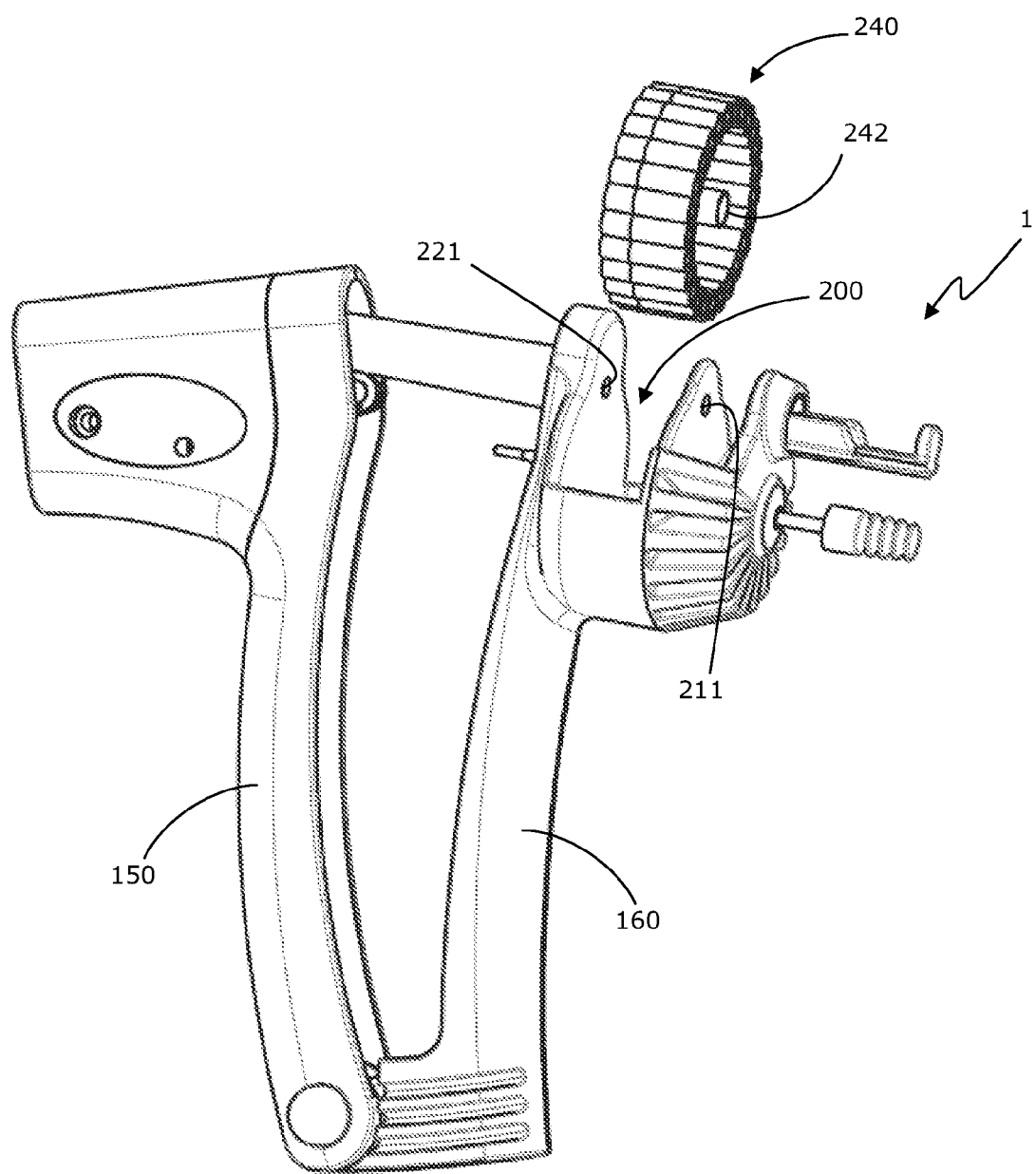
FIG. 5a is a perspective view of the tissue sampler with a collecting device magazine about to be placed into the magazine housing of the tissue sampler.
Figure 6:
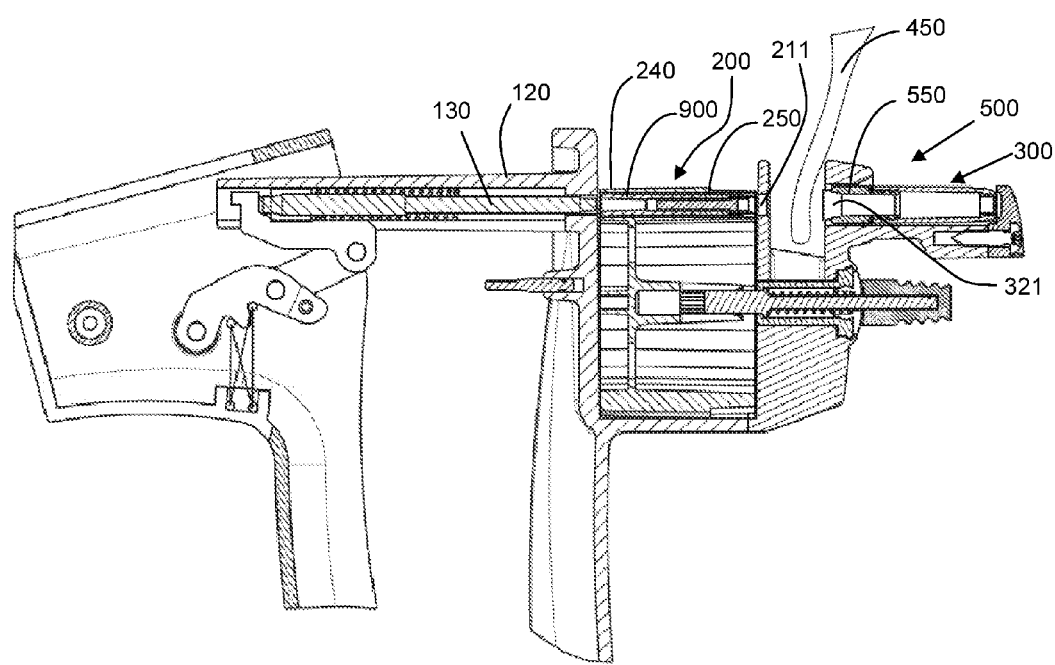
FIG. 6 is a cross-sectional side view of the tissue sampler of FIG. 5 in which an animal's ear is located in the cutting region.
Figure 6A:
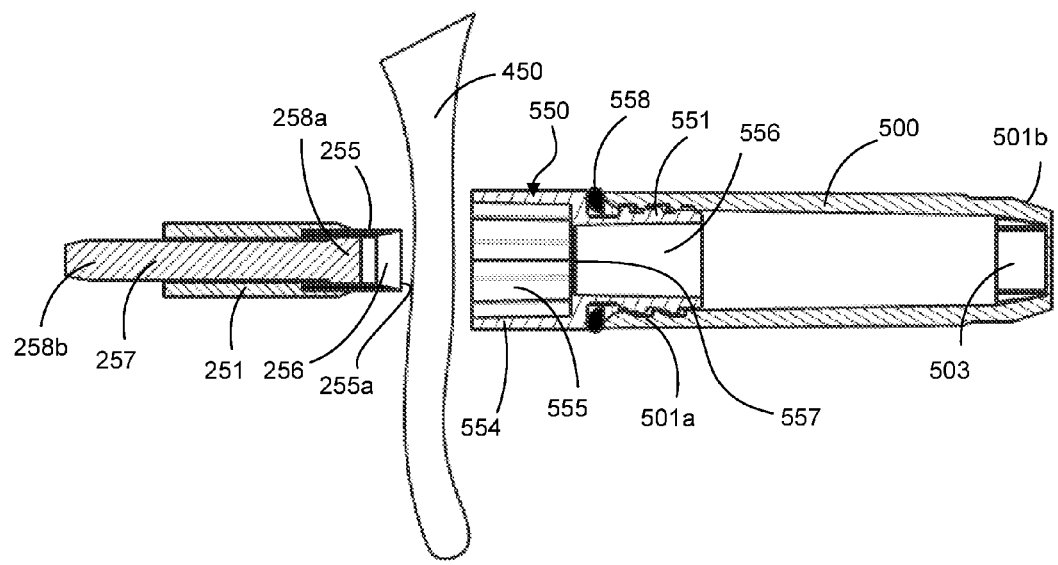
FIG. 6a is a cross-sectional side view of one form of collector before taking a tissue sample from an animal's ear and placing it into a storage container.
Figure 6B:
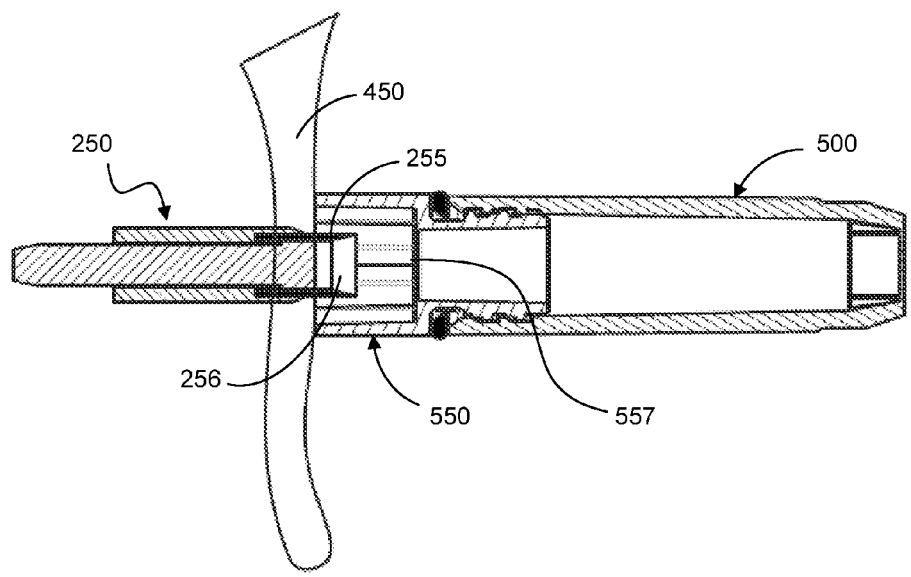
FIG. 6b is a cross-sectional side view of the collector of FIG. 6a when cutting a tissue sample from the animal's ear.
Figure 6C:
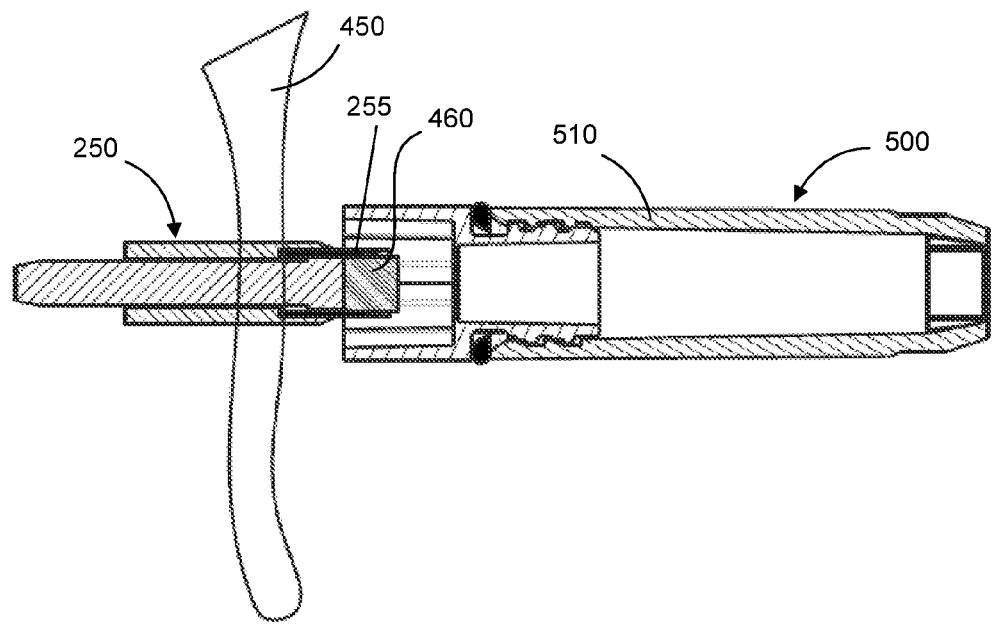
FIG. 6c is a cross-sectional side view of the collector of FIG. 6a after a tissue sample has been cut.
Figure 6D:
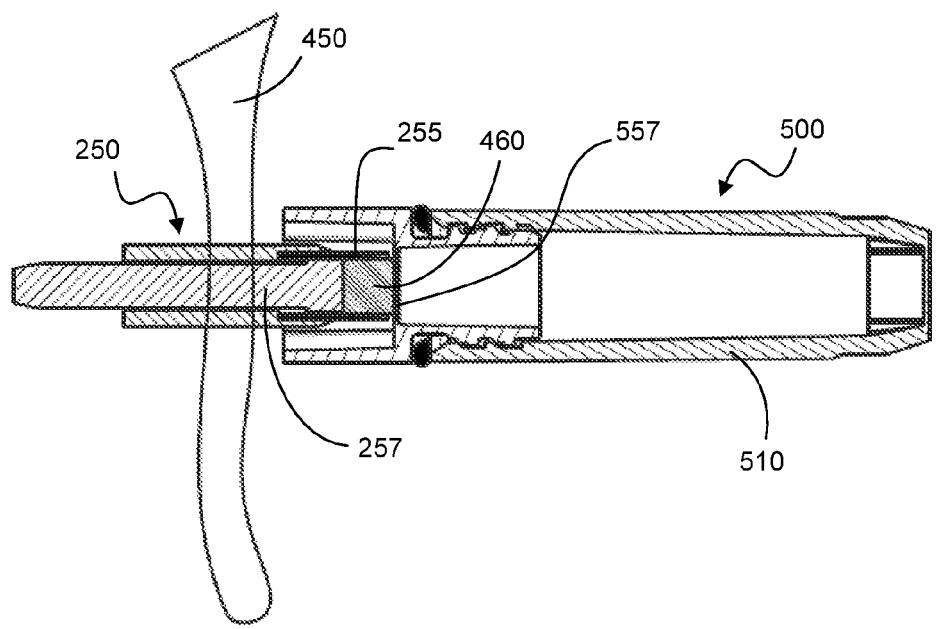
FIG. 6d is a cross-sectional side view of the collector of FIG. 6a pressing against a membrane in the cap of the storage container.
Figure 6E:
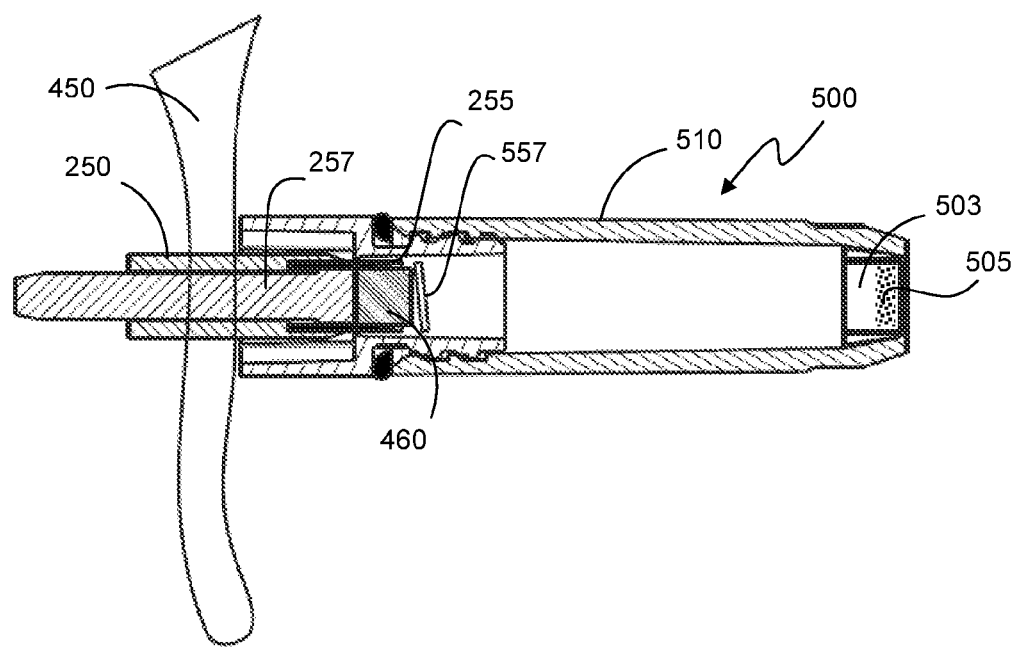
FIG. 6e is a cross-sectional side view of the collector of FIG. 6a after the membrane has been broken.
Figure 7A:
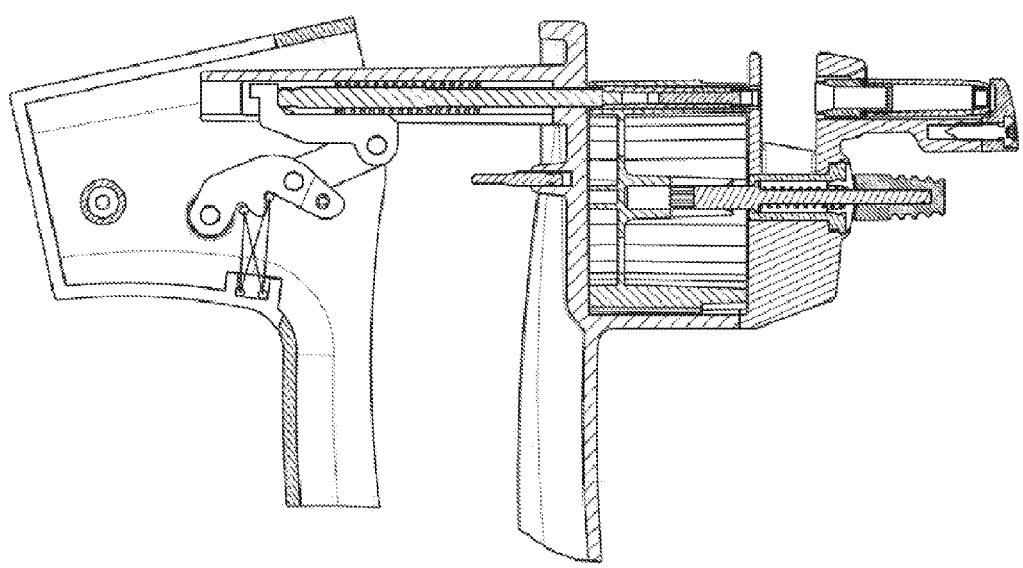
FIG. 7a is a cross-sectional side view of the tissue sampler of FIG. 6 in the ram is engaged with a shield and collector ready to cut a sample from the animal's ear.
Figure 7B:
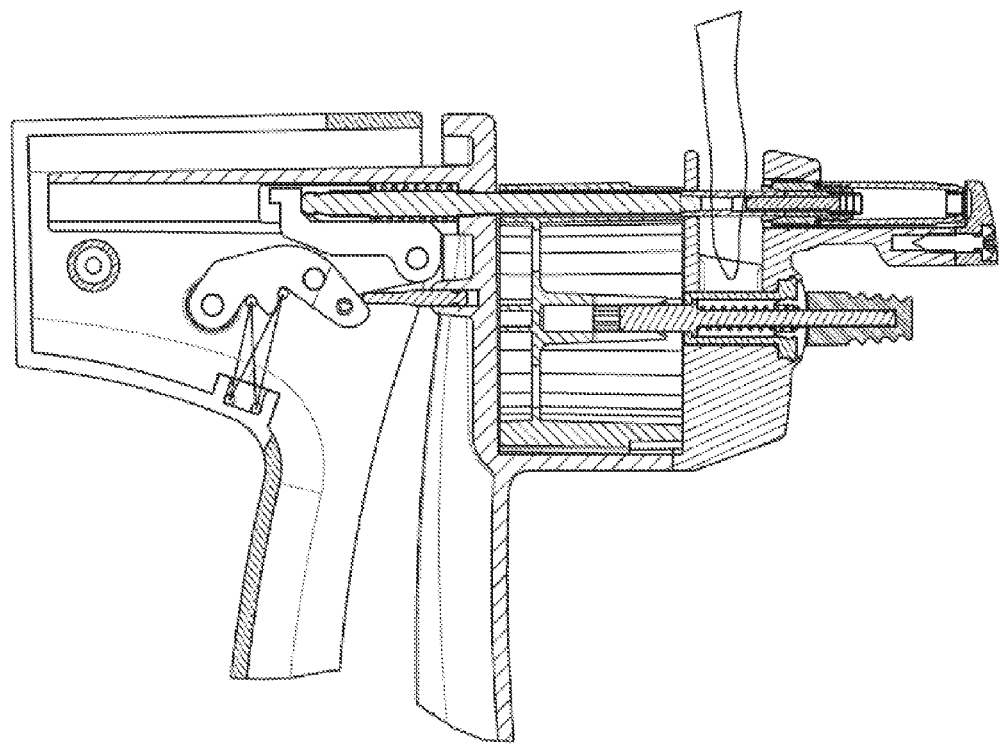
FIG. 7b is a cross-sectional side view of the tissue sampler of FIG. 6 in the ram is engaged with a shield and collector having cut a sample from the animal's ear.
Figure 7C:
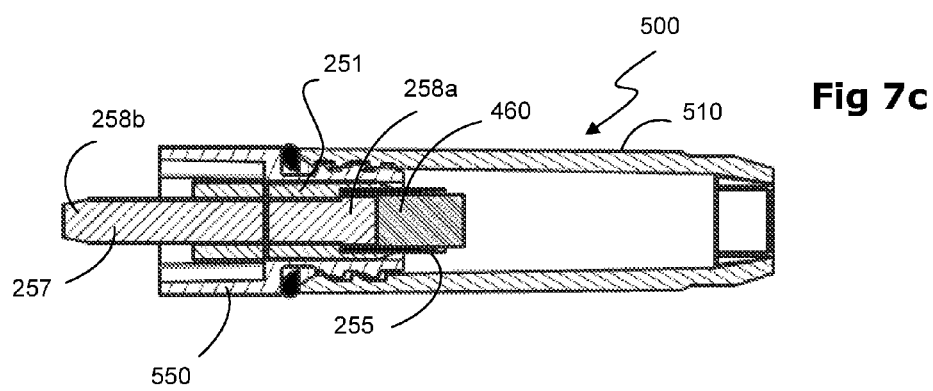
FIG. 7c is a cross-sectional side view of the collector of FIG. 6a in which it is plugging the first end of the storage container.
Figure 8:
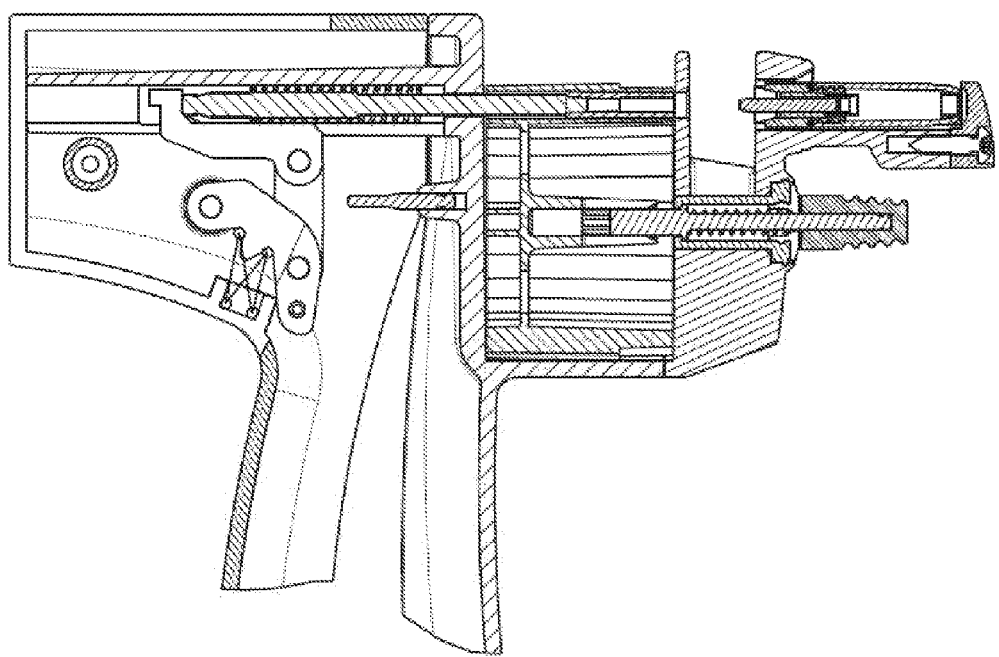
FIG. 8 is a cross-sectional side view of the tissue sampler of FIG. 6 in which the animal's ear is removed from the cutting region and the collector has plugged the storage container and the shield and ram are moving back to though the magazine
Figure 9:
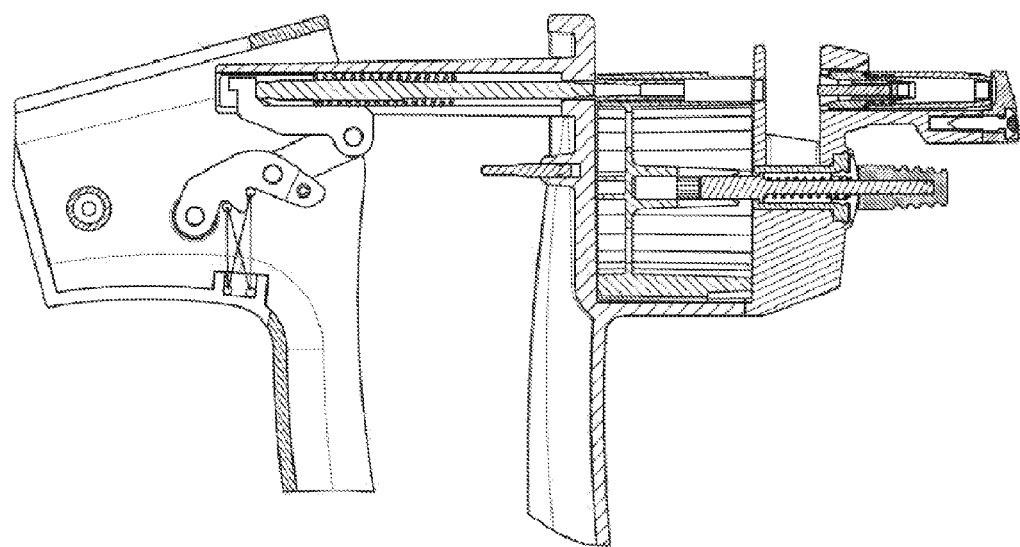
FIG. 9 is a cross-sectional side view of the tissue sampler of FIG. 6 in which the ram has been retracted through and is returned to its rest position having left behind a used shield in the magazine.

The storage container is dimensioned to fit within the storage container holder 300 of the tissue sampler 1 as shown in FIGS. 5 and 6 and to receive a collector through the first end of the storage container, as indicated in FIG. 4.

When a tissue sample is to be taken, a storage container 500 is placed in the container holder 300 so that its first end 501 faces toward the cutting region 400, as shown in FIG. 5.

A plurality of collectors 250 may be positioned within a magazine housing 200 loaded into the tissue sampler. The magazine can sequentially present each collector for sampling. This is achieved by aligning the collectors individually with an actuator such as a ram 130 of the sampler 1. To avoid or reduce the prospect of cross contamination, a shield 900 paired with each collector is also provided to cooperate with the ram and each collector. A shield is preferably pre-loaded in each chamber.

Such cross contamination is avoided by the provision of a shield 900 that separates the ram from coming into contact with the tissue surfaces.

The shield facilitates operation of the tissue sampler without bringing the ram of the tissue sampler into contact with the animal tissue. The shield acts as either an intermediary between the ram and the sample collector or as a shroud or cover for a portion of the ram that acts directly on the sample collector. The shield is disposable.

In the preferred form a shield 900 and a collector 250 are associated with each other in a chamber of the magazine.

Figure 11:
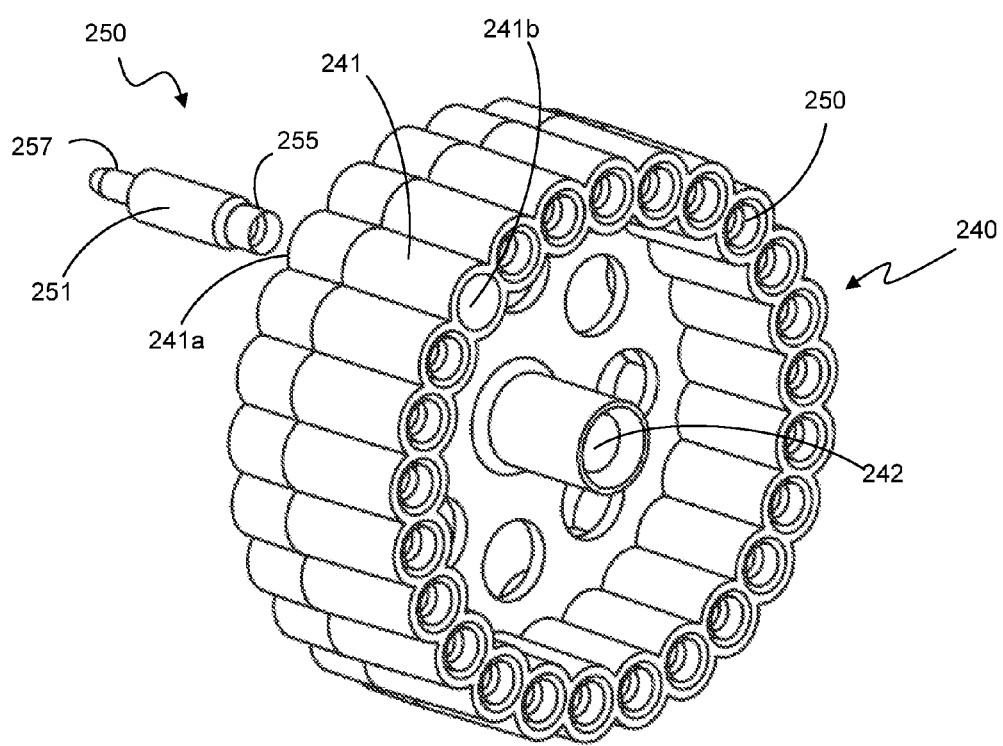
FIG. 11 is a perspective view of a magazine.
Figure 12:
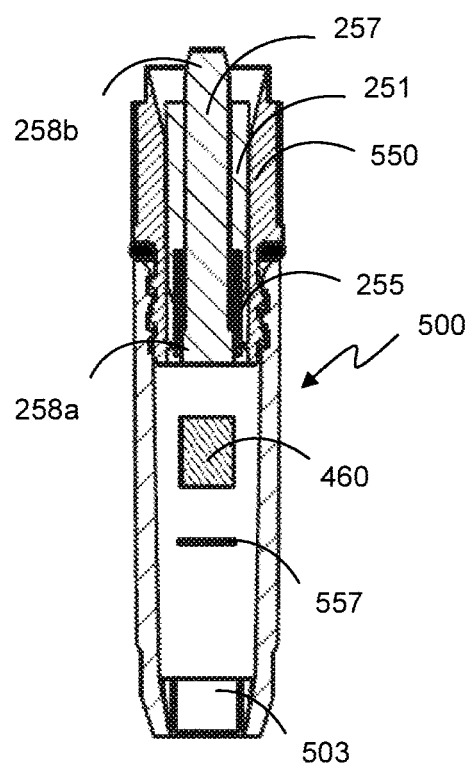
FIG. 12 is a cross-sectional side view of the storage container in which the tissue sample has been released from the collector.
Figure 13:
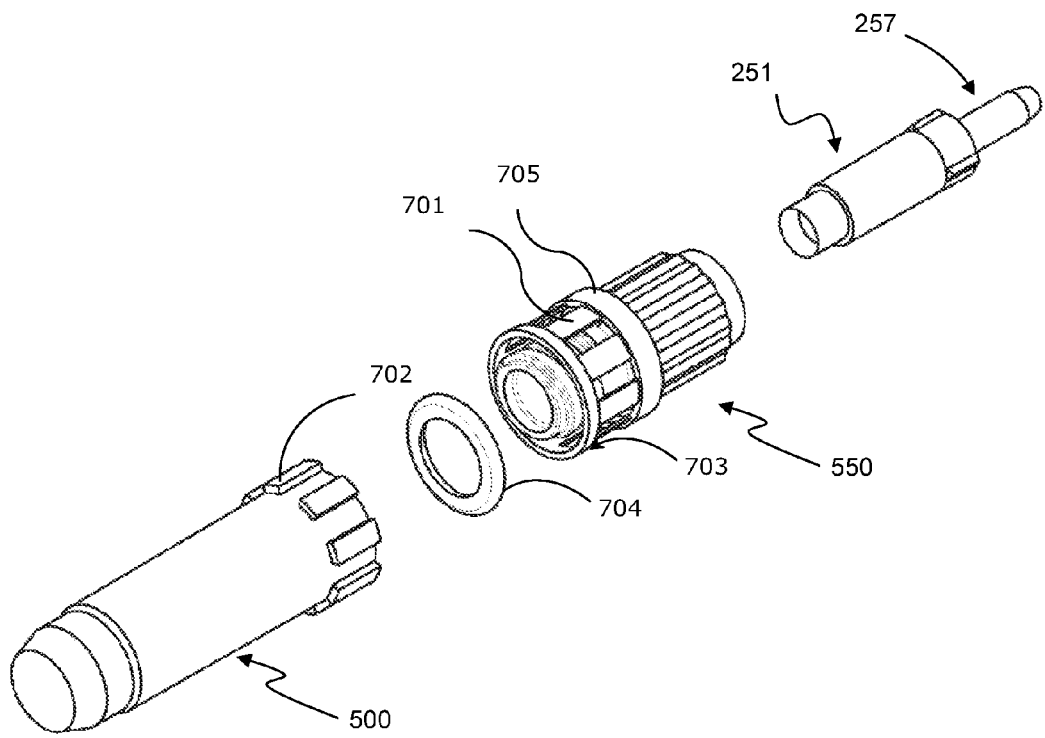
FIG. 13 is an exploded perspective view of a tamperproof collector and associated storage container.

As shown in FIG. 11, the magazine housing 200 is sized to receive a magazine 240 comprising a plurality of chambers 241, each chamber being adapted to hold a shield 900 and collector 250 therein and having open first and second opposing ends 241*a*, 241*b*. The magazine, is preferably in the form of a cylinder having a centrally located axle or bore 242 that extends through or into the magazine. The chambers are positioned concentrically around the bore and preferably near the circumference of the magazine. Preferably, at least a portion of the chambers in the magazine 240 is of a transparent material, so that the presence of a shield and/or collector in any of the chambers can be identified. In the embodiment shown in FIG. 11, the magazine comprises 25 chambers, although the magazine may have any suitable number of chambers. In the preferred form the magazine can rotate to index collectors for actuation. In other forms the magazine may translate instead.

In the preferred form of the tissue sampler the shield retracts from the cutting/penetration zone on withdrawal action of the ram. This leaves the portion of tissue being sampled, for example an animal ear, to be withdrawn from the penetration zone.

The shield may be included in conjunction with an associated collector for example in a cartridge or in the same slot in a magazine. Alternatively shields may be provided separately, as individual units to load into the tissue sampler, or in a cartridge or magazine of their own.

Initially the shield is located in a position between the ram and the collector. Activation of the ram on a driving stroke advances the ram, the moving ram engages a rear end of the shield.

A ram 130 is positioned within the ram housing 120 of the sampler. The ram forms part of an actuating means, which also comprises a trigger 150 operably connected to the ram 130. A guiding recess 132 is formed in the first end of the ram and is shaped to correspond with the second end 258*b* of the plunger, which projects from the punch. The guiding recess 132 is dimensioned so that the projecting portion of the plunger can fit within the recess and so that the first end of the ram 121*a* can push the pushing end 252*b* of the punch.

The ram 130 is adapted to slide back and forth within the ram housing 120 as the trigger 150 is engaged and disengaged.

To cut a tissue sample, a user inserts a storage container 500 into the holder 300 so that a portion of the storage container is pushed into the sampler receiving aperture 321 so that the first end of the storage container projects slightly from the sample receiving aperture 321 and into the cutting region, as shown in FIG. 6. The magazine 240 is orientated so that the cutting edge of a punch 251 of the active collecting device 250 is aligned with the cutting region aperture 211 and the second end of the plunger 257 is aligned with the ram receiving aperture 221. As will be appreciated, the magazine can be placed into the tissue sampler before or after the storage container is placed in the tissue sampler.

Upon being driven by the ram 130 both the shield and the collector 250 advance towards the storage container. As the ram pushes the collector through the cutting region, the cutting end of the punch pushes the animal's ear (or other tissue) against the first end of the storage cap and the first wall of the cutting region. The cutting edge of the punch is then pushed through the ear or other tissue to cut a sample plug from the tissue. At cutting the punch and cap act as a punch and die. The cap, its passage and/or seal act as a die to cooperate with the punch to facilitate a shear action removal of the sample.

As shown where the first end of the storage container 500 comprises a cap 550 with a seal 557 as described above, the collector 250 is pushed into the recess 555 formed in the cap.

Optionally, the wall of the recess comprises one or more ribs for engaging with the guiding ribs 254 of the punch to guide the body of the punch within the cap. As the collector pushes into the cap, the cutting edge 255a of the punch presses against and then pierces the seal or membrane 557 to form an opening to the storage body. The cutting end of the punch (holding the plunger therein) is then pushed through the opening so that the sample holding region 256, and the sample 460 held within the cavity 256, is located within the body of the storage container 500. The collector fills the opening formed by the broken seal to close off the first end of the container. In particular, the size of the punch is sized to fit snugly and preferably sealingly within the opening formed in the cap so that the cap is able to hold the collector therein. Preferably, the second end of the plunger projects from the pushing end of the punch and the first end of the plunger is located within the bore of the punch between the sample holding cavity and the pushing end of the punch. In this arrangement, the plunger can be depressed and pushed through the sample holding region to release the tissue sample into the storage container. This may occur manually or by tool and may be done at sampling or after. When the collector closes off the first end of the storage container, the punch and the plunger are held by the cap of the storage container so that the cutter is held within the container body. It remains so during transport to a laboratory. It is therefore not necessary for the user of the sampler to handle the punch with its sharp cutting edge or to otherwise remove and discard the punch from the tissue sampler.

The trigger mechanism of the sampler 1 is such that the action of cutting the tissue sample, placing the sample in the storage container, and releasing the animal's ear is almost instantaneous so that if the animal reacts to having its ear cut and pulls away, there is little chance that the animal can pull the tissue sampler from the user's hand before the ear is released.

Figure 10A:
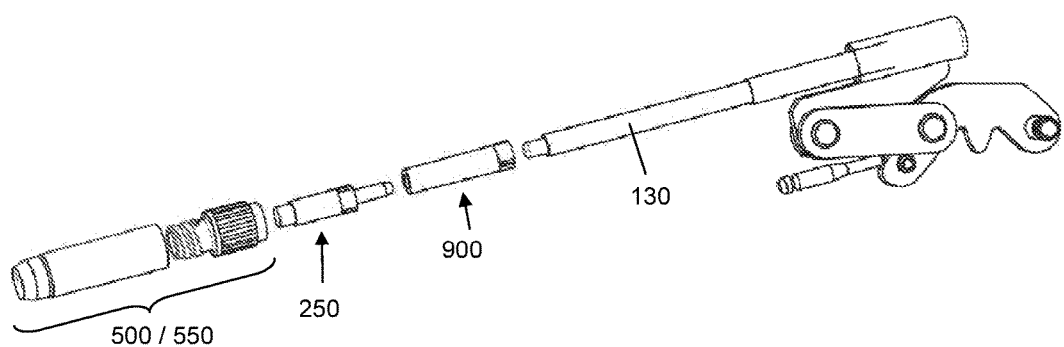
FIG. 10a is an exploded perspective view of part of the sampler and the shield together with the collector and storage container.
Figure 10B:
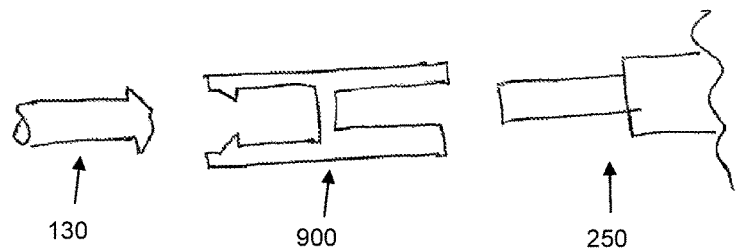
FIG. 10b is a partial sectional view of the ram, shield and collector.
Figure 10C:
FIG. 10c is sectional view of a ram, shield and collector of one form.
Figure 10D:
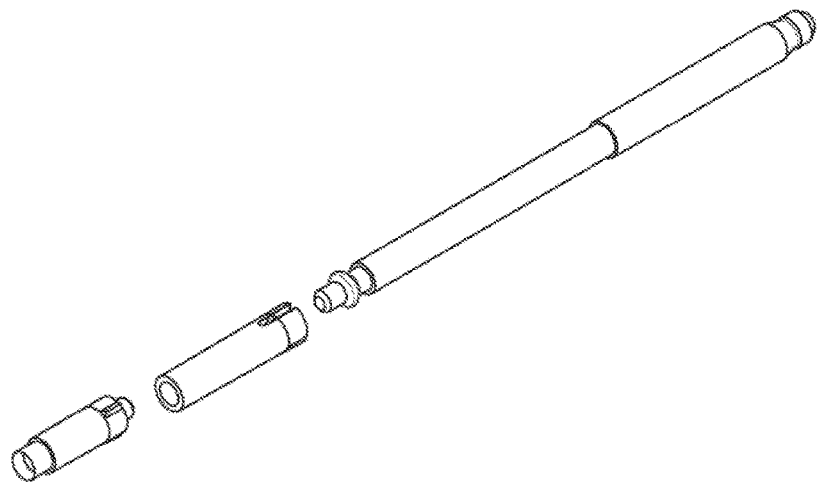
FIG. 10d is an exploder perspective view of the ram, shield and collector of FIG. 10c.
Figure 10E:
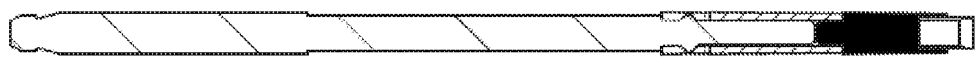
FIG. 10e is sectional view of a ram, shield and collector of another form.
Figure 10F:
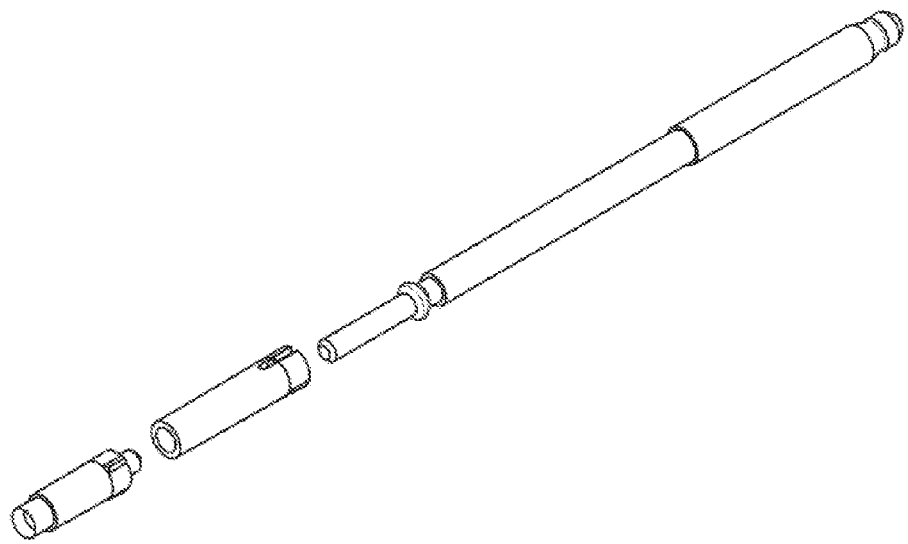
FIG. 10f is an exploder perspective view of the ram, shield and collector of FIG. 10e.

In one form of shield seen in FIGS. 10e and 10f, a leading portion of the ram passes through a passage in the shield and acts on the sample collector to drive it through the penetration zone. In this form the shield covers the end of the ram, and so protects the ram from contact with the tissue. In another form of shield (illustrated in FIG. 10a-10d), the leading portion of the ram acts on the shield, which in turn acts on the sample collector to drive it through the penetration zone. In this form the ram does not enter the penetration zone, and all contact with the tissue by the retractable part of the mechanism is made by the shield. Alternatively the shield may be a combination, where the ram acts on the shield which acts in turn on the sample collector, but where the ram also enters an interior space of the shield over a portion of its length and may enter the penetration zone over this shielded portion.

In both forms of FIGS. 10a-10f the shield preferably includes features at a forward end to engage with the sample collector. For example the shield may include a socket which engages over any plunger at the rear end of the sample collector. The engagement may be formed to be sufficiently stable to maintain the two parts as a single unit during actuation, without the unit buckling under compressive loads. Alternatively, or as well, the length dimension of the shield, the collector, or both may be sufficiently greater than the breadth of the penetration zone that the components are supported by the housing of the tissue sampler at one end, the other end or both ends during actuation.

In both forms, the shield preferably includes features at a rear end to engage with the ram. These features are arranged to allow the ram to pick up and connect to the shield when moving in the advance direction. So the engagement force is less than the force exerted by the collector on either a tissue being sampled or an anvil surface to ensure correct engagement. These features also allow disengagement of the ram from the shield on withdrawal of the ram. During withdrawal the shield preferably engages the housing and stops, while continued movement of the ram disengages the ram from the shield. The engagement features are chosen such that disconnection force of the ram from the shield is greater than the disconnection force of the shield from the sample collector, but lower than the withdrawal force acting on the ram at this point in its travel.

The connection features between the ram and the shield in the illustrated forms may be provided by flexible fingers at the rear of the shield which engage over a sloped rib on the body of the ram. The fingers include gripping lugs on the inward surface. In use the fingers flex outward to pass the rib as the ram enters the rear end of the shield. The fingers flex back to position. The expected release force is determined by the angle of the surfaces and the stiffness of the fingers.

The rear end of the shield buts against an aperture of the housing from which the ram extends in actuation. As the shield does not fit into the aperture, the shield is stripped from the end of the ram as the ram withdraws further into the housing.

For convenient use a shield may be supplied preassembled to the rear end of each sample collector.

For convenient use the combined shield and collector assemblies may be provided in a magazine carrying a large number of such assemblies, for example more than 10. The magazine may be located for use in the tissue sampling tool in a magazine loading zone between the ram (in the withdrawn position) and the penetration zone. In use the magazine carrying a plurality of sample collectors is manipulated to selectively present a combined shield and collector in the path of the ram. On actuation the ram enters the cartridge and engages the shield. The combination is moved from the magazine through the penetration zone.

The disposable shield returns to the magazine preferably to its original position on withdrawal of the ram after actuation. The shield releases from the ram upon full withdrawal of the shield into the magazine and by continuing withdrawal motion of the ram. Once the magazine of collectors is fully used, the magazine, with its collection of contaminated shields, may be discarded as a unit.

In some forms, the sample collector includes a body and a plunger actuable within the body, with actuation of the plunger releasing a sample from the sample collector. For these forms, the shield is formed so that neither the ram nor the spacer actuate the plunger in pressing the sample collector through the penetration zone. For example the bearing surface of the shield (or of the ram) that acts on the collector may be annular, acting around the perimeter of the rear end of the collector.

In some forms the disposable shield is longer than the breadth of the penetration zone, so that the collector may be fully driven through the penetration zone, without exposing any portion of the ram in the penetration zone.

The disposable shield may be a similar length overall to the sample collector.

Whilst in the preferred form the shield and collector is provided located in a magazine of a plurality of shields and collectors it is envisaged that single shot assemblies of a collector and shield may be provided. The advantage of a magazine located collector and shield is that once all of the collectors have been dispensed from the magazine the retracted shields are then retained by the magazine and can be disposed of in an appropriate manner as a single unit.

The storage container, including the cap holding the collector can then be removed from the holder and an unused replacement storage container can then be fitted into the holder. The collector magazine is rotated incrementally until the next chamber containing an unused collector and shield is aligned with the ram receiving aperture and cutting region aperture, ready for another tissue sample to be taken by a fresh collector.

Once all the collectors in the magazine have been used the magazine with used shields can be removed from the sampler 1.

What we claim is:

1. A biopsy sampler comprising:
   a penetration zone for receiving a part of an organism to be sampled,
   a ram situated at a first side of the penetration zone, the ram able to be actuated to move along a path between a withdrawn position and an advanced position,
   a sample collector that can cut a biopsy sample from tissue from said part interposed in the penetration zone, and a container that can receive the sample collector, the sample collector and the container being initially located on opposite sides of the penetration zone to each other,
   a disposable shield initially located between the ram and the penetration zone, when the ram is in the withdrawn position,
   an advance action of the ram from the withdrawn position to the advanced position brings the sample collector to the container, so the sample collector and the container are together at a side of the penetration zone away from the ram, and brings the disposable shield into the penetration zone,
   a withdrawal action of the ram from the advanced position to the withdrawn position withdrawing the disposable shield to the first side of the penetration zone, leaving the tissue free to leave the penetration zone,
   such that in use in collecting a sample the disposable shield contacts tissue surfaces and the ram does not contact tissue surfaces, and
   wherein the disposable shield is releasably fitted to the sample collector in an initial condition, and releasably connects to a leading end of the ram as the ram advances, and disconnects from the sample collector as the ram begins to withdraw, and disconnects from the ram as or before the ram reaches the withdrawn position on withdrawal.

2. A biopsy sampler as claimed in claim 1 wherein the disposable shield is a sleeve to receive a leading end of the ram, and protects the leading end of the ram from contacting the tissue surfaces as the leading end of the ram enters the penetration zone.

3. A biopsy sampler as claimed in claim 2 wherein the sleeve is open through both ends such that the leading end of the ram may act directly on the sample collector or container.

4. A biopsy sampler as claimed in claim 1 wherein the disposable shield spaces the ram from the sample collector or container and the ram acts to bring the sample collector and container together by acting on the shield which acts on the sample collector or container.

5. A biopsy sampler as claimed in claim 4 wherein travel of the ram is limited so that the ram cannot enter the penetration zone.

6. A biopsy sampler as claimed in claim 1 wherein the sample collector is initially located between the ram and the penetration zone.

7. A biopsy sampler as claimed in claim 1 wherein the connection of the ram to the shield is stronger than a connection of the shield to the sample collector such that withdrawal of the ram reliably releases the shield from the sample collector.

8. A biopsy sampler as claimed in claim 6 including a magazine loading zone between the ram, when the ram is in the withdrawn position and the penetration zone, and a magazine locatable in the magazine loading zone, the magazine carrying a plurality of sample collectors to be selectively presented in the path of the ram and be actuated by the ram to be moved from the magazine through the penetration zone, each sample collector being stored in the magazine in association with a respective disposable shield, the disposable shield returning to the magazine on withdrawal of the ram after actuation.

9. A biopsy sampler as claimed in claim 8 wherein the shield releases from the ram upon full withdrawal of the shield into the magazine and by continuing withdrawal motion of the ram.

10. A biopsy sampler as claimed in claim 9 wherein the ram projects through an aperture in the advanced position but not in the withdrawn position, and the shield does not fit into the aperture so that during withdrawal of the ram with an attached shield, the shield butts against a periphery of the aperture and further withdrawal of the ram disengages the shield from the ram.

11. A biopsy sampler as claimed in claim 8 wherein the shield has a first connection interface with the collector, the shield has a second connection interface with the ram and the collector has a connection interface engages a vial or cover upon actuation of the ram to take a sample, the collector to vial or cover interface having a greater disconnection force than the shield to collector interface, and the shield to collector interface having a lower disconnection force than the shield to ram interface.

12. A biopsy sampler as claimed in claim 1 wherein the sample collector includes a body and a plunger actuable within the body, actuation of the plunger releasing a sample from the sample collector, and neither the ram nor the spacer actuate the plunger in pressing the sample collector through the penetration zone.

13. A biopsy sampler as claimed in claim 1 wherein the disposable shield is longer than a distance between the sides of the penetration zone.

* * * * *